US006726898B2

(12) United States Patent
Jernberg

(10) Patent No.: US 6,726,898 B2
(45) Date of Patent: Apr. 27, 2004

(54) LOCAL DELIVERY OF AGENTS FOR DISRUPTION AND INHIBITION OF BACTERIAL BIOFILM FOR TREATMENT OF PERIODONTAL DISEASE

(76) Inventor: Gary R. Jernberg, 2283 Northridge Dr., N. Mankato, MN (US) 56003

( * ) Notice: Subject to any disclaimer, the term of this patent is extended or adjusted under 35 U.S.C. 154(b) by 0 days.

(21) Appl. No.: 10/456,696

(22) Filed: Jun. 6, 2003

(65) Prior Publication Data

US 2003/0219387 A1 Nov. 27, 2003

Related U.S. Application Data

(63) Continuation-in-part of application No. 09/715,514, filed on Nov. 17, 2000, now Pat. No. 6,576,226.
(51) Int. Cl.[7] ............................. A61K 7/16; A61K 9/14; A61K 38/16; A61K 31/40; A61K 31/34
(52) U.S. Cl. ......................... 424/49; 424/401; 424/489; 424/490; 514/6; 514/424; 514/472
(58) Field of Search ........................... 424/49–58, 401, 424/489, 490; 514/6, 424, 472

(56) References Cited

U.S. PATENT DOCUMENTS

| 4,636,524 | A | 1/1987 | Balazs et al. |
|---|---|---|---|
| 4,685,883 | A | 8/1987 | Jernberg |
| 4,736,024 | A | 4/1988 | Della Valle et al. |
| 4,764,377 | A | 8/1988 | Goodson |
| 4,780,320 | A | 10/1988 | Baker |
| 4,851,521 | A | 7/1989 | della Valle et al. |
| 4,919,939 | A | 4/1990 | Baker |
| 4,937,254 | A | 6/1990 | Sheffield et al. |
| 4,957,744 | A | 9/1990 | della Valle et al. |
| 5,059,123 | A | 10/1991 | Jernberg |
| 5,095,037 | A | 3/1992 | Iwamitsu et al. |
| 5,166,331 | A | 11/1992 | della Valle et al. |
| 5,197,882 | A | 3/1993 | Jernberg |
| 5,202,431 | A | 4/1993 | della Valle et al. |
| 5,225,205 | A | 7/1993 | Orsolini |
| 5,236,355 | A | 8/1993 | Brizzolara et al. |
| 5,275,820 | A | 1/1994 | Chang |
| 5,290,271 | A | 3/1994 | Jernberg |
| 5,324,520 | A | 6/1994 | Dunn et al. |
| 5,336,767 | A | 8/1994 | della Valle et al. |
| 5,340,849 | A | 8/1994 | Dunn et al. |
| 5,366,733 | A | 11/1994 | Brizzolara et al. |
| 5,384,333 | A | 1/1995 | Davis et al. |
| 5,451,406 | A | 9/1995 | Lawin et al. |
| 5,466,462 | A | 11/1995 | Rosenthal et al. |
| 5,466,465 | A | 11/1995 | Royds et al. |
| 5,500,228 | A | 3/1996 | Lawter et al. |
| 5,514,379 | A | 5/1996 | Weissleder et al. |
| 5,536,508 | A | 7/1996 | Canal et al. |
| 5,540,912 | A | 7/1996 | Roorda et al. |
| 5,622,498 | A | 4/1997 | Brizzolara et al. |
| 5,626,838 | A | 5/1997 | Cavanaugh, Jr. |
| 5,631,228 | A | 5/1997 | Oppenheim et al. |
| 5,639,738 | A | 6/1997 | Falk et al. |
| 5,644,049 | A | 7/1997 | Giusti et al. |
| 5,646,119 | A | 7/1997 | Oppenheim et al. |
| 5,646,129 | A | 7/1997 | Callegaro et al. |
| 5,660,854 | A | 8/1997 | Haynes et al. |
| 5,672,351 | A | 9/1997 | Chikindas et al. |
| 5,696,078 | A | 12/1997 | Oppenheim et al. |
| 5,886,965 | A | 3/1999 | Tozaki et al. |
| 5,912,230 | A | 6/1999 | Oppenheim et al. |
| 6,153,210 | A | 11/2000 | Roberts et al. |
| 6,193,994 | B1 | 2/2001 | Lee et al. |
| 6,309,669 | B1 | 10/2001 | Setterstrom et al. |
| 6,319,510 | B1 | 11/2001 | Yates |

FOREIGN PATENT DOCUMENTS

| CA | 2285673 | 4/2001 |
|---|---|---|
| JP | 404182420 | 6/1992 |
| JP | 6-105901 A | 4/1994 |
| JP | 07267868 A | 10/1995 |
| JP | 08151326 A | 6/1996 |
| WO | WO 93/16732 | 9/1993 |
| WO | WO 93/16733 | 9/1993 |
| WO | WO 94/04058 | 3/1994 |
| WO | WO 94/07505 | 4/1994 |
| WO | WO 99/014312 | 3/1999 |
| WO | WO 00/067917 | 11/2000 |
| WO | WO 00/103727 | 1/2001 |
| WO | 01/056627 | 8/2001 |

OTHER PUBLICATIONS

Asaria, R.H.Y. et al., "Biofilm on Scleral Explants with and Without Clinical Infection", *Retina, The Journal of Retinal and Vitreous Diseases,* vol. 19, No. 5, pp. 447–450 (1999).

Brown, M. et al., "Relationship Between Glycocalyx and Providone–Iodine Resistance in *Pseudomonas aeruginosa* (ATCC 27853) Biofilms", *Appl. Environ. Microbiol.,* vol. 61, No. 1, pp. 187–193 (1995).

Burne, R. et al., "Physiologic Homeostasis and Stress Responses in Oral Biofilms", *Physiology,* pp. 441–460 (Date Unknown).

Cook, GS. et al., Biofilm Formation by *Porphyromonas gingivalis* and *Streptococcus gordonii*, *J. Periodont. Res.,* vol. 33, pp. 323–327 (1998).

Costerton, J. et al., "Mechanism of Electrical Enhancement of Efficacy of Antibotics in Killing Biofilm Bacteria", *Antimicrob. Agents Chemother.,* vol. 38, No. 12, pp. 2803–2809 (Dec. 1994).

Costerton, J.W. et al., "Bacterial Biofilms: A Common Cause of Persistent Infections", *Science,* vol. 284, pp. 1318–1322 (May 21, 1999).

(List continued on next page.)

*Primary Examiner*—Raymond J. Henley, III
(74) *Attorney, Agent, or Firm*—Merchant & Gould P.C.

(57) ABSTRACT

The present invention relates to compositions and methods of treating periodontal disease and related disorders utilizing a sustained, controlled release targeted delivery method to effectively disrupt and inhibit bacterial biofilms at periodontal treatment sites.

8 Claims, 2 Drawing Sheets

OTHER PUBLICATIONS

Costerton, J.W., "Original Article. Introduction to Biofilm", *International Journal of Antimicrobial Agents,* vol. 11, pp. 217–221 (1999).

Costerton, J.W., "The Role of Bacterial Exopolysaccharides in Nature and Disease", *Journal of Industrial Microbiology & Biotechnology,* vol. 22, pp. 551–563 (1999).

Dunn, et al., "Sustained release of cisplatin in dogs from an injectable implant delivery system", *Journal of Bioactive and Compatible Polymers,* Oct. 1996; 11:286–300.

Ehrhart, et al., "The Effects of a controlled–release cisplatin delivery system after marginal resection of breast carcinoma", Univ. of Illinois at Urbana–Champaign, Urbana, IL, 1997.

ELAttar, et al., "Arachidonic acid metabolism in inflamed gingiva and its inhibition by anti–inflammatory drugs", *J. Periodontol.* 1984; 55:536–539.

Feldman, et al., "Non–steroidal anti–inflammatory drugs in the reduction of human alveolar bone loss", *J. Clinical Periodontol.* 1983; 10:131–136.

Fletcher, J. et al., "Cytokine Degradation by Biofilms of *Porphyromonas gingivalis*", *Current Microbiology,* vol. 36, pp. 216–219 (1998).

Genco, "Antibiotics in the treatment of human periodontal diseases", *J. Periodontol* 1981; 52:545–558.

Golub, et al., "Tetracyclines inhibit tissue collagenase activity—A new mechanism in the treatment of periodontal disease", *J. Periodont Res.* 1984; 19:651–655.

Golub, et al., "Tetracylclines inhibit tissue collagenases. Effects of ingested low–dose and local delivery systems", *J. Periodontol* 1985; 56 (Suppl.):93–97.

Goodson, "A potential role of prostaglandins in the etiology of periodontal disease", *Prostaglandins and Cyclic AMP, Academic Pres,* New York, 1973; 215–216.

Goodson, et al., "Periodontal therapy by local delivery of tetracycline", *J. Clin Periodontol* 1979, 6:83–92.

Helmerhorst, E.J. et al., "The Effects of Histatin–derived Basic Antimicrobial Peptides on Oral Biofilms", *J. Dent. Res.* vol. 78, No. 6, pp. 1245–1250 (Jun. 1999).

Holland, S. et al., "Biofilm and Scleral Buckle–associated Infections. A Mechanism for Peristance", *Ophthalmology,* vol. 98, No. 6, pp. 933–938 (Jun. 1991).

James, S. et al., "Purification and Characterization of a Novel Antibacterial Protein from the Marine Bacterium D2", *Appl. Environ. Microbiol.,* vol. 62, No. 8, pp. 2783–2788 (Aug. 1996).

Jayaraman, A. et al., "Corrosion Inhibition by Acrobic Biofilms on SAE 1018 Steel", *Appl. Microbiol. Biotechnol.,* vol. 47, pp. 62–68 (1977).

Kolenbrander, P. et al., "Spatial Organization of Oral Bacteria in Biofilms", *Methods in Enzymology,* vol. 310, pp. 322–332 (1999).

Lana, et al., "Slow release cisplatin combined with radiation for the treatment of canine nasal tumors", 1996.

Lewis, et al., Eds., *NSAIDs in Periodontol Disease,* Chapter 9: "Nonsteroidal anti–inflammatory drugs in Periodontal disease", by R. C. Williams; Marcel Dekker, Inc., New York, 1987, pp. 143–155.

Licking, E., "Getting a Grip on Bacterial Slime", *Business Week,* pp. 98, 100 (Sep. 13, 1999).

Lillehei, et al., "Efficacy of intralesionally administered cisplatin–impregnated biodegradable polymer for the treatment of 9L gliosarcoma in the rat", *Neurosurgery,* Dec. 1996; 39(6):1191–1199.

Lindhe, et al., "Local tetracycline delivery using hollow fiber devices in periodontal therapy", *J. Clin Periodontol* 1979; 6:141–149.

Owusu–Ababio, G. et al., "Effectiveness of Ciprofloxacin Microspheres in Eradicating Bacterial Biofilm", *Journal of Controlled Release,* vol. 57, pp. 151–159 (1999).

Schluger, et al., Eds., *Periodontal Diseases,* 2nd Ed, Chapter 8: "Pathogenic Mechanisms", Lea & Febiger, 1990; pp. 221–262.

Srinivasan, S. et al., "Extracellular Signal Molecule(s) Involved in the Carbon Starvation Response of Marine Vibrio sp. Strain S14", *J. Bacteriol.,* vol. 180, No. 2, pp. 201–209 (Jan. 1998).

Straw, et al., "Effects of cis–diamminedichloroplatinum II released from D,L–polylactic acid implanted adjacent to cortical allografts in dogs", *J Orthop Res,* 1994; 12(6):871–877.

Vogel, et al., "The effects of topical steroidal and systemic non–steroidal anti–inflammatory drugs on experimental gingivitis in man", *J. Periodontol* 1984; 55:247–251.

Waite, et al, "The periodontal status of subjects receiving nonsteroidal anti–inflammatory drugs", *J. Periodont Res* 1981; 16:100–108.

Weaks–Dybvig, et al., "The effect of indomethacin on alveolar bone loss in experimental periodontitis", *J. Periodont Res,* 1982; 17:90–100.

Williams, et al, "Altering the progression of human alveolar bone loss with the non–steroidal anti–inflammtory drug flurbiprofen", *J. Periodontol* 1989; 60(9):485–490.

Williams, et al., "Host modulation in the management of periodontal diseases", *Amer. Acad. Periodontol,* Apr. 1990 (7 pgs).

Williams, et al., "Topical flurbiprofen treatment of periodontitis in beagles", *J. Periodont. Res.* 1988; 23:166–169.

Wilson, M. et al., "Effect of Phenoxyethanol, Chlorhexidine and their Combination on Subgingival Plaque Bacteria", *Journal of Antimicrobial Chemotherapy,* vol. 25, pp. 921–929 (1990).

Wilson, M. et al., "Isolation and Identification of Bacteria from Subgingival Plaque with Low Susceptibility to Minocycline", *Journal of Antimicrobiol. Chemotherapy,* vol. 28, pp. 71–78 (1991).

Wilson, M., "Susceptibility of Oral Bacterial Biofilms to Antimicrobial Agents", *J. Med. Microbiol.,* vol. 44, pp. 79–87 (1996).

Wilson, M., "Use of Constant Depth Film Fermentor in Studies of Biofilms of Oral Bacteria", *Methods in Enzymology,* vol. 310, pp. 264–279 (1999).

Withrow, et al., "Slow release adjuvant cisplatin for treatment of metastatic canine osteosarcoma", *Eur J Exp Musculoskel Res* 1995; 4:105–110.

Wood, P. et al., "Surface–catalysed Disinfection of thick *Pseudomonas aeruginosa* Biofilms", *Journal of Applied Microbiology,* vol. 84, pp. 1092–1098 (1998).

"Proceedings from the state of the art workshop on surgical therapy for periodontitis", *J. Periodontol* 1982; 53(8):475–501.

LOCAL DELIVERY OF AGENTS FOR DISRUPTION AND INHIBITION OF BACTERIAL BIOFILM FOR TREATMENT OF PERIODONTAL DISEASE

CROSS REFERENCE TO RELATED APPLICATION

The present application is a continuation in part of U.S. patent application Ser. No. 09/715,514, filed Nov. 17, 2000, and issued Jun. 10, 2003 as U.S. Pat. No. 6,576,226, which application and patent are incorporated herein by reference.

TECHNICAL FIELD OF THE INVENTION

The present invention relates to compositions and methods of treating periodontal disease and related disorders utilizing a sustained, controlled release targeted delivery method to effectively disrupt and inhibit bacterial biofilms at periodontal treatment sites.

BACKGROUND OF THE INVENTION

Periodontal diseases are a major affliction to mankind. Gingivitis, inflammation of gingival (gum) tissue, and periodontitis, inflammation and progressive loss of ligament and alveolar (socket) bone support to teeth, are caused by bacteria which colonize tooth surfaces and occupy the gingival crevice area. These are major periodontal disease afflictions worldwide. Bacterial plaque is the principal causative agent of these periodontal diseases.

Routine daily prevention or removal of plaque by the patient is a cornerstone of periodontal therapy. Toothbrushes, dental floss and various other oral hygiene instruments can be used. These devices require motor skill and dexterity. The daily routines for adequate plaque removal require the patient to be diligent, motivated, educated and skillful. Accordingly, such methods are effective only when used by motivated individuals and then often to a limited extent.

Optimal response of the immune system to defend against bacterial assault is often not realized in patients prone to periodontal disease and the immune response may actually contribute to the disease process.

Conventional periodontal therapy has emphasized mechanical removal of soft and hard accretions of bacteria (i.e., plaque and calculus) from the root surface via use of dental instruments placed into the gingival crevice to mechanically shear the accretions from the tooth structure. See S. Kakehashi and P. F. Parakkal, *Proceedings from the State of Art Workshop on Surgical Therapy for Periodontitis*, J. Periodontal 53:475 (1982). However, scaling and root planning is often only partially effective in the removal of these accretions. Moreover, the removal is transient and the bacteria re-colonize the root surface.

Adjunctive therapies have been suggested for the treatment of periodontal diseases. Systemic antibiotics have been used in the periodontal therapy. See R. J. Genco, *Antibiotics in the Treatment of Human Periodontal Diseases*, J. Periodontal 52:545 (1981). However, systemic delivery (e.g., oral or intramuscular) typically does not provide a sufficient concentration of antibiotic over an extended period of time to the gingival crevice area.

Applicant's U.S. Pat. No. 4,685,883 deals with controlled sustained release of chemotherapeutic agents in a bioerodable matrix in the periodontal pocket lesion via placement of the matrix in the periodontal pocket lesion with dental instruments. In one embodiment, the chemotherapeutic agents are incorporated into microspheres. These agents, although in sufficient concentration in the gingival crevice or periodontal pocket lesion, may not be able to adequately penetrate into the mass of the residual bacterial accretions on the tooth surfaces. Moreover, the bacterial accretions can rapidly reform.

Although specific bacteria are essential agents for many periodontal disease, their presence alone on the tooth surface and underneath the gingiva is not sufficient to explain the periodontal disease process. Rather, the host must react to this bacterial challenge if disease is to develop and progress. As with other bacterial infections, the host's immune system acts locally at the invasion site and attempts rapidly to neutralize, remove, or destroy the bacterial agents. In periodontal disease, however, chronic bacterial plaque accumulation causes an excessive and persistent antigenic stimulus. Therefore, the host response, rather than being protective and self-limiting, can be destructive. See R. C. Page, *Periodontal Disease*, p. 221, Lea and Febiger, Philadelphia, 1989.

Applicant's U.S. Pat. No. 5,939,047 deals with a controlled release topical delivery system to facilitate absorption and deposition of host immune system modulating agents into the gingival and oral mucosal tissues adjacent to the periodontium to dampen deleterious effects of host cell immune response to the periodontal bacteria challenge. If the bacterial challenge remains persistent, however, the host immune response can remain excessive and persistent.

Recent attention has been given to removing unwanted biofilms forming in various industrial processes. Biofilms are notoriously resistant to removal. The tendency of bacteria to adhere, secrete an adhesive extracellular matrix and grow is a strong evolutionary advantage difficult to overcome. So far, little success has been realized. Observation of living bacterial biofilms by modern methods has established that these microbial populations form a very complicated structural architecture. See, e.g., J.W. Costerton, et al., *Microbial biofilms*, Annu. Rev. Microbial, 49:711 (1995). This suggested the operation of a cell—cell signaling mechanism for bacteria to produce these complex structures. After twenty years of research, it is generally assumed now that all enteric bacteria and gram negative bacteria are capable of cell density regulation using acylated homoserine lactones (AHLs) as autoinducer molecules.

In early stages a biofilm is comprised of a cell layer attached to a surface. The cells grow and divide, forming a dense mat numerous layers thick. When sufficient numbers of bacteria are present (quorum) they signal each other to reorganize forming an array of pillars and irregular surface structures, all connected by convoluted channels that deliver food and remove waste. The biofilm produces a glycocalyx matrix shielding them from the environment. Urinary tract and urinary catheter infections are examples of biofilm infections.

As the biofilm matures, the bacteria become greatly more resistant to antibiotics than when in the planktonic (free cell) state. See H. Anwar, et al, *Establishment of aging biofilms: a possible mechanism of bacterial resistance to antimicrobial therapy*, Antimicrob Agents Chemother 36:1347 (1992). The host immune system is also significantly less effective against bacteria in the biofilm state. See E. T. Jensen, et al, *Human polymorphonuclear leukocyte response to Pseudomonas aeruginosa biofilms*, Infect Immun 5:2383 (1990). Certain bacterial strains may be able to confer resistance protecting the biofilm from host defense components that would otherwise bind to the surface of viable bacteria and kill them. See D. Grenier and M. Belanger, *Protective effect of Porphyromonas gingivalis outer membrane vesicles against bactericidal activity of human serum*, Infect Immun 59:3004 (1991). Yet the bacterial biofilm exudes lipopolysaccharide agitating the host inflammatory response which, in periodontitis, contributes to the tissue destruction.

For Gram-negative bacteria, the signal components in quorum sensing are autoinducers, acylated homoserine lactones (AHLs). These highly membrane-permeable compounds diffuse out of and into the cells and accumulate in localized environments, as the growing population of bacteria increases. At a threshold concentration the autoinducers trigger gene transcription in the localized population of bacteria, activating biochemical pathways and physiological functions appropriate for growth and survival of the bacteria in that environment. Agents which can inhibit AHLs would be beneficial in biofilm disruption or inhibition. See, e.g., S. Srinivasan, et al, *Extracellular signal molecule(s) involved in the carbon starvation response of marine vibrio sp. strain S14*, J. Bacteriol 180:201 (1998).

Production of another novel signaling molecule is also regulated by changes in environmental conditions associated with a shift from a free-living existence to a colonizing or pathogenic existence in a host organism. This signal molecule is termed autoinducer-2. See, e.g., B. L. Bassler et al., U.S. Patent Application No. 20020107364.

Targeting specific bacteria for inhibition or exclusion from biofilm colonization would be beneficial in creating a more favorable bacterial ecology in the periodontal pocket. For example, gingipains are trypsin-like cysteine proteinases produced by *Porphyromonas gingivalis*, a major causative bacterium of adult periodontitis. Gingipains play a role in bacterial housekeeping and infection, including amino acid uptake from host proteins and fimbriae maturation.

The present invention solves these and other problems by optimal delivery of biofilm disruption and inhibition agents at localized periodontal treatment sites.

SUMMARY OF THE INVENTION

The present invention relates to the use of time release biodegradable microshapes for sustained, controlled, targeted delivery of agents to disrupt and inhibit the formation of biofilms at localized periodontal treatment sites. The method involves the insertion of biodegradable microshapes containing agents active against bacterial biofilms into the gingival crevice or periodontal pocket region.

In one embodiment of the present invention, biodegradable, time-release microspheres containing agents generally disruptive of bacterial biofilms are delivered by a syringe or other dental instrument. In another embodiment of the present invention, microspheres containing agents generally inhibitive of bacterial biofilms are delivered similarly.

In yet another embodiment of the present invention, biodegradable, time-release microspheres containing agents disruptive to specific bacteria within the biofilm are delivered by a syringe or dental instrument. In another embodiment of the present invention, microspheres containing agents which inhibit colonization of specific bacteria within the biofilms are similarly delivered.

In still another embodiment of the present invention, agents having other methods of action (antibiotics, host modulation agents, etc.) are delivered in microspheres along with agents in microspheres effective against the biofilm by syringe or dental instrument. These agents have synergy in their effectiveness with this embodiment of the present invention.

These and various other advantages and features of novelty which characterize the invention are pointed out with particularity in the claims annexed hereto and forming a part hereof. However, for a better understanding of the invention, its advantages and objectives obtained by its use, reference should be made to the drawings which form a further part hereof, and to the accompanying descriptive matter in which there is illustrated and described preferred embodiments of the invention.

BRIEF DESCRIPTION OF THE DRAWINGS

In the drawings, in which like reference numerals and letters indicate corresponding parts throughout the several views.

DETAILED DESCRIPTION OF THE INVENTION

Figure 1A:
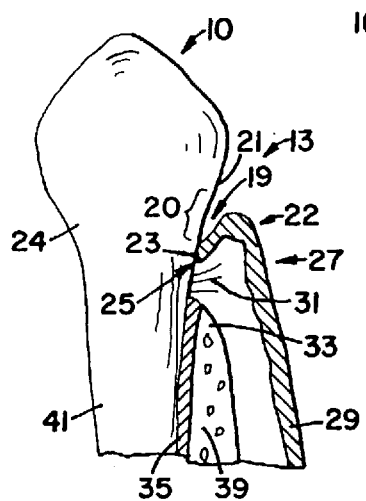
FIGS. 1A through 1C are diagrammatic views illustrating the human periodontal anatomy, including an illustration of the healthy human periodontium in FIG. 1A, an illustration of the effects of gingivitis in FIG. 1B, and an illustration of the effects of periodontitis in FIG. 1C.

The present invention relates to a method for release of agents that disrupt or inhibit bacterial biofilms at localized sites in the mouth. The present method can include local delivery of bacterial biofilm inhibitor or disruptor agents to localized sites in the mouth for treatment of periodontal disease. The present method can employ inserting biodegradable microparticles containing the agents into the periodontal pocket, allowing the microparticles to degrade, and releasing the agents in a controlled, sustained manner. In an embodiment, the method includes inserting using a syringe apparatus or hand delivery device.

In an embodiment, the method employs agents that inhibit or disrupt the glycocalyx matrix of the bacterial biofilm. In an embodiment, the method employs agents that are antagonists of acylated homoserine lactones. In an embodiment, the method employs agents that are furanones or furanone derivatives. In an embodiment, the method employs agents that inhibit specific bacteria from inhabiting the bacterial biofilm. In an embodiment, the method employs agents that bind with or inhibit bacterial lipopolysaccharide. In an embodiment, the method employs agents that are histatin analogues.

In an embodiment, the method employs other chemotherapeutic agents also. These chemotherapeutic agents can be microencapsulated and combined with microencapsulated bacterial biofilm inhibitors or disruptors for insertion into the periodontal pocket. In an embodiment, the method employs chemotherapeutic agents selected from the group consisting of antibiotics, anti-inflammatory agents, and anti-collagenolytic agents.

In an embodiment, the method employs biodegradable microparticles configured as microspheres between 10 and 700 microns in diameter.

Bacteria employ a cell—cell signaling mechanism for bacteria to produce biofilms. For example, it is generally believed that all enteric bacteria and gram negative bacteria are capable of cell density regulation using acylated homoserine lactones (AHLs) as autoinducer molecules. Agents which can inhibit AHLs would be beneficial in biofilm disruption or inhibition. In an embodiment, the method employs agents that are antagonists of acylated homoserine lactones. In an embodiment, the present method employs certain furanones as antagonists of AHLs. In an embodiment, the present method employs agents that inhibit autoinducer-2.

When sufficient numbers of bacteria are present (quorum) they signal each other to reorganize forming an array of pillars and irregular surface structures, all connected by convoluted channels that deliver food and remove waste. Such a biofilm includes a glycocalyx matrix shielding the microbes from the environment. In an embodiment, the method employs agents that inhibit or disrupt the glycocalyx matrix of the bacterial biofilm.

Lactoferrin is an iron-binding salivary protein that has been shown to reduce binding of cells in its iron-saturated form. In an embodiment, the method employs iron saturated lactoferrin to disrupt or inhibit biofilm.

Gingipains are bacterial proteinases with a functional role in infection and pathogenesis of periodontitis. Gingipain inhibitors can be agents for periodontal disease therapy. DX-9065a can inhibit gingipain. DX-9065a selectively reduces *P. gingivalis* growth, suggesting a potential therapeutic effect of gingipain inhibitors on periodontitis. In an embodiment, the present method employs an agent that is a gingipain inhibitor. In an embodiment, the present method employs DX-9065a to disrupt or inhibit biofilm.

Synthetic histatin analogues have shown potential for reduction of viable bacterial counts in the oral biofilm model. dhvar 4 shows action against Gram-negative bacteria. A possible explanation for this finding is that dhvar 4 binds to the negatively charged lipopolysaccharide (LPS) moiety, which is specific for Gram-negative bacteria. Certain Gram-negative bacteria are involved in the development of periodontal disease. The involvement of LPS in the initial binding of amphipathic basis antimicrobial peptides to the bacterial membrane has been reported. Furthermore, comparison of the amino acid sequence of dhvar 4 with bactericidal/permeability-increasing protein (BPI) revealed that the N-terminal 5 amino acids of dhvar 4 show strong homology with the LPS binding domain of BPI. See E. J. Helmerhorst, et al, *The effects of histatin-derived basic antimicrobial peptides on oral biofilms*, J. Dent Res 78: 1245 (1999).

In an embodiment, the method employs agents that are furanones or furanone derivatives.

Suitable furanones are disclosed in U.S. Pat. Nos. 6,337,347 and 6,455,031, the disclosures of which are incorporated by reference. Such furanones include compounds of Formula 1 or Formula 2:

Formula 1

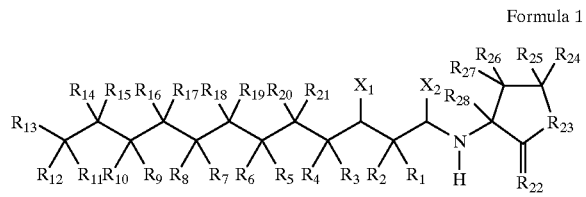

Formula 2

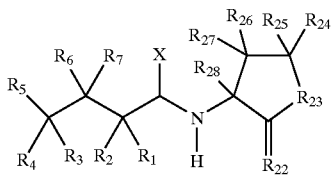

In Formulas 1 or 2, $R_1$–$R_{21}$ can independently be H, $C_1$–$C_4$ alkyl group (preferably $CH_3$), OH, $NH_2$, SH, or halogen (e.g., F, Cl, Br, or I); $R_{22}$ and $R_{23}$ can independently be H, S, O, and N (e.g., NR or NH), preferably S or O; $R_{24}$–$R_{28}$ can independently be H or halogen; and X, $X_1$, and $X_2$ can independently be O, S, $H_2$, or any combination of H plus one halogen or two halogens when one or more R groups is substituted. The furanone can be an optically active isomer.

In an embodiment, the furanone has Formula 1. In an embodiment of Formula 1, at least one of $R_1$–$R_{21}$ is halogen, or the alkylene chain of the molecule contains a sulfur in the chain.

In an embodiment of Formula 1, $R_{24}$–$R_{28}$ are H or halogen, and $R_{22}$–$R_{23}$ are H. In an embodiment of Formula 1, one or more carbons forming the backbone of the molecule are substituted with S or S-substituted moieties. In an embodiment of Formula 1, $X_1$ and/or $X_2$ is $H_2$, H plus halogen, or two halogens. In an embodiment of Formula 1, $R_{22}$ is H, S, O or NH and $R_{23}$ is S, O, or N. In an embodiment of Formula 1, the alkylene side chain contains one or more double bonds or triple bonds between carbon atoms within the alkylene side chain. In an embodiment of Formula 1, X1–X2 is H2; H plus a halogen; two halogens; H plus OH or $NH_2$; or a double bonded O, NH, or S.

In an embodiment, the furanone has Formula 2. In an embodiment of Formula 2, at least one of $R_1$–$R_7$ is halogen, or the alkylene chain of the molecule contains a sulfur in the chain. In an embodiment of Formula 2, $R_{22}$ is H, S, O or NH and $R_{23}$ is S, O, or N. In an embodiment of Formula 2, the alkylene side chain contains one or more double bonds or triple bonds between carbon atoms within the alkylene side chain. In an embodiment of Formula 2, X is H2; H plus a halogen; two halogens; H plus OH or NH2; or a double bonded O, NH, or S.

The furanones of Formulas 1 or 2 can also include the above structures with modifications such as: 1) Alteration of the acyl side chain by increasing or decreasing its length. 2) Alteration of the structure of the acyl side chain, such as addition of a double bond or a triple bond between carbon atoms within the acyl side chain. 3) Substitution on carbons in the acyl side chain, e.g., the addition of a methyl group or other group such as an oxo-group, a hydroxyl group, an amino group, a sulfur atom, a halogen or dihalogen or some other atom or R-group to any location along the acyl side chain. 4) Substitution of carbons comprising the backbone of the acyl side chain with S or S substituted moieties or with N or N substituted moieties. 5) Substitution on the homoserine lactone ring portion of the molecule. For example: addition of a sulfur group to produce a thiolactone. 6) Halogenated acyl furanones have been shown to act as blockers to homoserine lactone cognate receptor proteins. 7) Ring size of the acyl side chain varying heterocylic moiety is variable. For example, 4-membered and 6-membered rings containing nitrogen (i.e., beta and delta lactams) are included.

The furanones of Formulas 1 and 2 include compounds such as compounds 1–12:

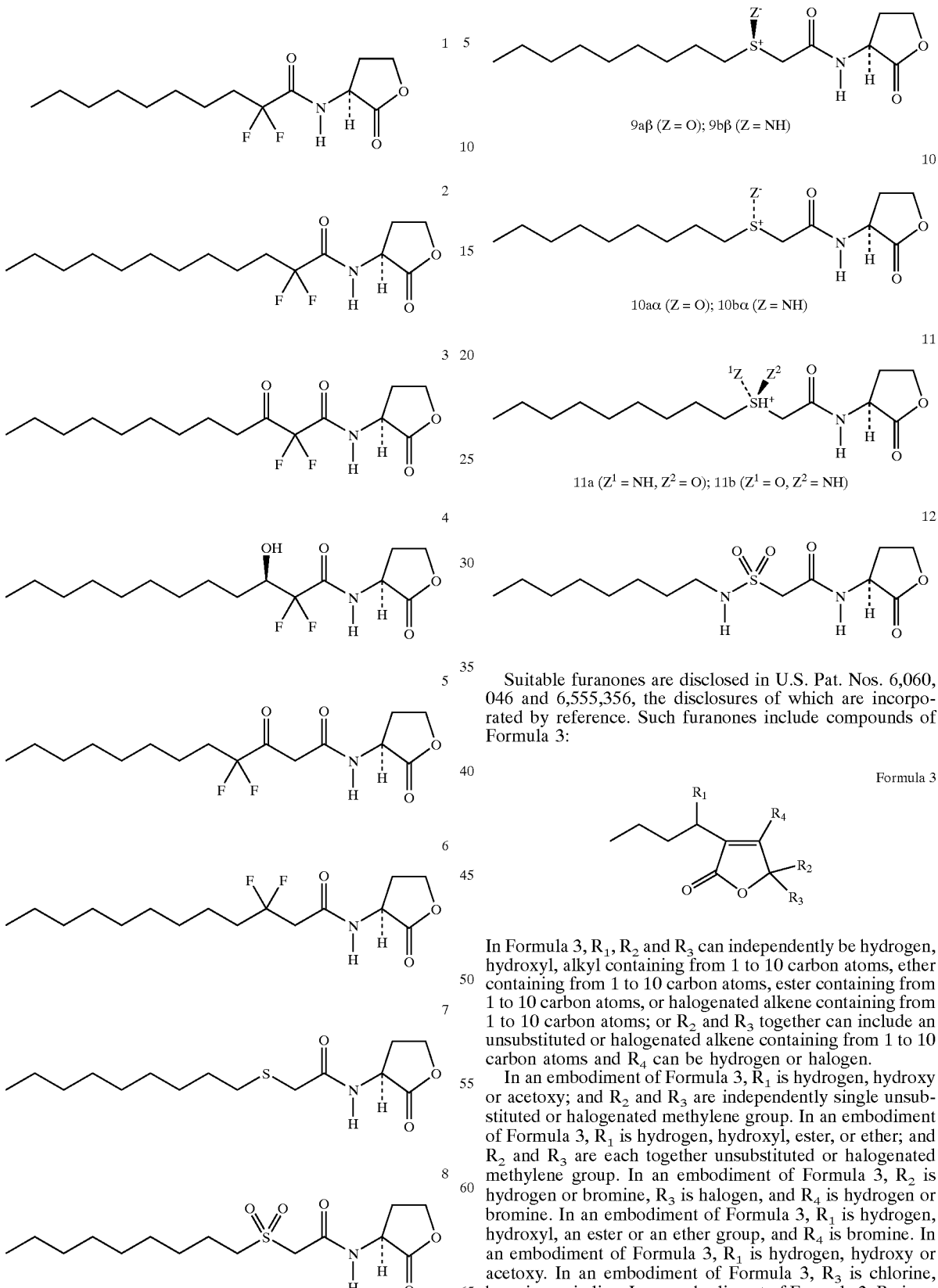

Suitable furanones are disclosed in U.S. Pat. Nos. 6,060,046 and 6,555,356, the disclosures of which are incorporated by reference. Such furanones include compounds of Formula 3:

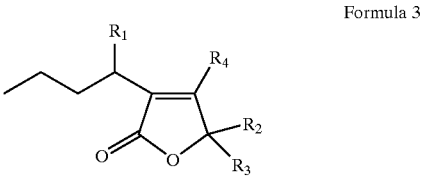

Formula 3

In Formula 3, $R_1$, $R_2$ and $R_3$ can independently be hydrogen, hydroxyl, alkyl containing from 1 to 10 carbon atoms, ether containing from 1 to 10 carbon atoms, ester containing from 1 to 10 carbon atoms, or halogenated alkene containing from 1 to 10 carbon atoms; or $R_2$ and $R_3$ together can include an unsubstituted or halogenated alkene containing from 1 to 10 carbon atoms and $R_4$ can be hydrogen or halogen.

In an embodiment of Formula 3, $R_1$ is hydrogen, hydroxy or acetoxy; and $R_2$ and $R_3$ are independently single unsubstituted or halogenated methylene group. In an embodiment of Formula 3, $R_1$ is hydrogen, hydroxyl, ester, or ether; and $R_2$ and $R_3$ are each together unsubstituted or halogenated methylene group. In an embodiment of Formula 3, $R_2$ is hydrogen or bromine, $R_3$ is halogen, and $R_4$ is hydrogen or bromine. In an embodiment of Formula 3, $R_1$ is hydrogen, hydroxyl, an ester or an ether group, and $R_4$ is bromine. In an embodiment of Formula 3, $R_1$ is hydrogen, hydroxy or acetoxy. In an embodiment of Formula 3, $R_3$ is chlorine, bromine or iodine. In an embodiment of Formula 3, $R_1$ is an acetyl group. In an embodiment of Formula 3, $R_1$ is a hydroxy group and $R_2$ and $R_3$ are each bromine.

In an embodiment, the furanone has Formula 4:

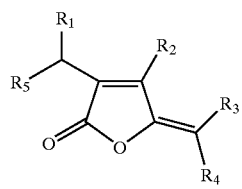

Formula 4

In Formula 4, $R_1$ is hydrogen, hydroxyl, acetoxy, ester or ether; $R_2$ is Br or H; $R_3$ and $R_4$ are independently hydrogen or halogen; and $R_5$ is $C_1$, $C_3$, $C_5$, or $C_{11}$ alkyl.

In an embodiment of Formula 4, $R_1$ is H, $R_2$ is Br, $R_3$ is Br, $R_4$ is Br, and $R_5$ is $C_3$ alkyl. In an embodiment of Formula 4, $R_1$ is H, $R_2$ is Br, $R_3$ is H, $R_4$ is Br, and $R_5$ is $C_3$ alkyl. In an embodiment of Formula 4, R is OAc, $R_2$ is Br, $R_3$ is H, $R_4$ is Br, and $R_5$ is $C_3$ alkyl. In an embodiment of Formula 4, $R_1$ is OH, $R_2$ is Br, $R_3$ is H, $R_4$ is Br, and $R_5$ is $C_3$ alkyl. In an embodiment of Formula 4, $R_1$ is OAc, $R_2$ is Br, $R_3$ is H, $R_4$ is I, and $R_5$ is $C_3$ alkyl. In an embodiment of Formula 4, $R_1$ is H, $R_2$ is H, $R_3$ is Br, $R_4$ is Br, and $R_5$ is $C_3$ alkyl. In an embodiment of Formula 4, $R_1$ is OAc, $R_2$ is Br, $R_3$ is Br, $R_4$ is Br, and $R_5$ is $C_3$ alkyl. In an embodiment of Formula 4, $R_1$ is H, $R_2$ is Br, $R_3$ is Br, $R_4$ is Br, and $R_5$ is $C_1$ alkyl. In an embodiment of Formula 4, $R_1$ is H, $R_2$ is Br, $R_3$ is H, $R_4$ is Br, and $R_5$ is $C_1$ alkyl. In an embodiment of Formula 4, $R_1$ is H, $R_2$ is H, $R_3$ is Br, $R_4$ is Br, and $R_5$ is $C_1$ alkyl. In an embodiment of Formula 4, $R_1$ is H, $R_2$ is Br, $R_3$ is H, $R_4$ is Br, and $R_5$ is $C_5$ alkyl. In an embodiment of Formula 4, $R_1$ is H, $R_2$ is H, $R_3$ is Br, $R_4$ is Br, and $R_5$ is $C_5$ alkyl. In an embodiment of Formula 4, $R_1$ is H, $R_2$ is H, $R_3$ is Br, $R_4$ is Br, and $R_5$ is $C_{11}$ alkyl.

In an embodiment, the furanone has Formula 5:

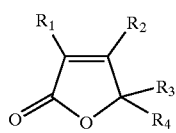

Formula 5

In Formula 5, $R_1$, $R_2$, $R_3$ and $R_4$ are each independently hydrogen, halogen, hydroxyl, methyl, alkyl, ether or ester.

Figure 1B:
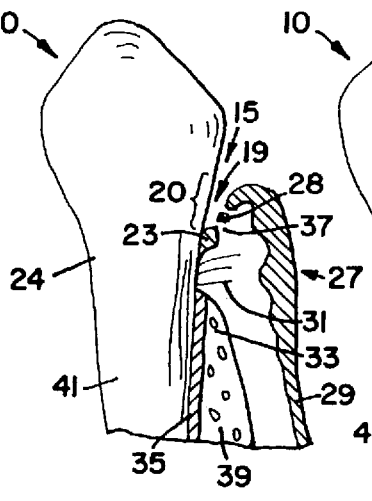
Figure 1C:
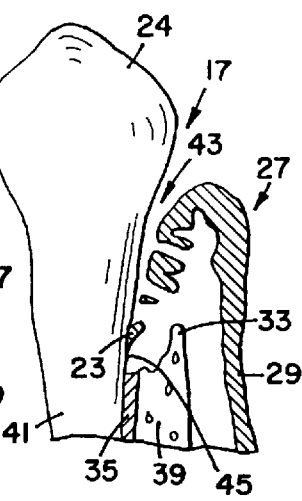
Figure 3:
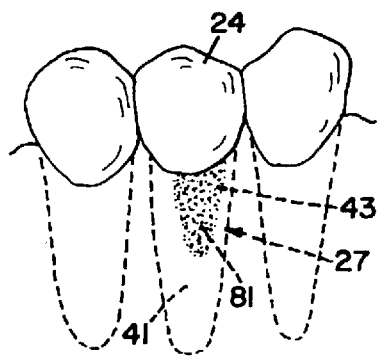
FIG. 3 is a partial diagrammatic view illustrating the placement into a periodontal pocket lesion, between the tooth and gingiva, of microencapsulated agent effective against the plaque biofilm.

Referring now to FIGS. 1A through 1C, wherein there is diagrammatically illustrated a human periodontal anatomy 10, progressing from a healthy human periodontium 13 illustrated in FIG. 1A to a periodontium afflicted with periodontitis 17 illustrated in FIG. 1C.

Specifically, FIG. 1A illustrates a healthy human periodontium 13. Between the gingival margin 21 and the free gingiva 22 is the healthy gingival sulcus or crevice 19. The depth 20 of the gingival sulcus or crevice 19, from the gingival margin 21 to the attachment of the junctional epithelium 23, is approximately 1–3 millimeters. The junctional epithelium attaches to the tooth 24 at the cementoenamel junction (CEJ) 25. The gingival tissues 27, including the epithelium 29 and gingival fibers 31, are healthy and without inflammation. The alveolar bone crest 33 and periodontal ligament are undamaged.

FIG. 1B illustrates the human periodontium afflicted with gingivitis 15. The gingival tissues 27 show signs of inflammation and crevicular ulceration 37, resulting in white cell infiltration into the gingival sulcus or crevice 19. Furthermore, the ulcerations 37 in the crevicular epithelium 28 result in bleeding upon provocation, such as through brushing and flossing or mastication.

FIG. 1C illustrates the human periodontium afflicted with periodontitis 17. The gingival tissues 27 are inflamed. The alveolar bone crest 33 and periodontal ligament 35 have broken down due to both bacterial and host defense factors. The breakdown of the attachment of the alveolar bone 39 and periodontal ligament 35 to the tooth root 41 has resulted in the formation of a periodontal pocket lesion 43. In addition, apical proliferation of the junctional epithelium 23 is noted along the root surface 45. A chronic white cell infiltrate in the periodontal pocket lesion 43 is persistent. If left untreated, the continual loss of alveolar bone tissue 39 would result in the loss of the tooth 24.

Figure 2:
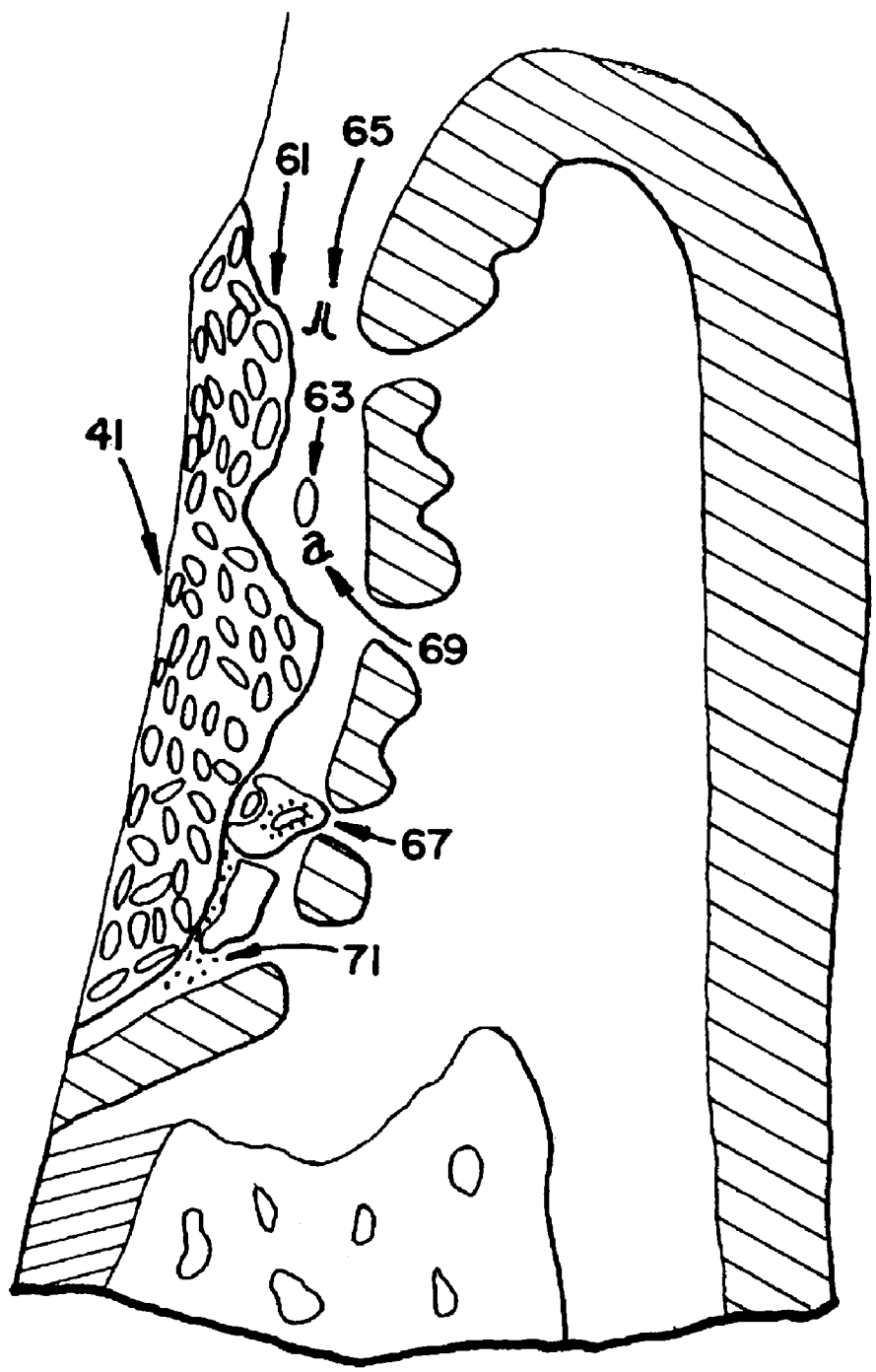
FIG. 2 is a diagrammatic view of dental plaque biofilm on a tooth root surface.

FIG. 2 illustrates dental plaque biofilm 61 on a tooth surface 41. Planktonic bacteria 63 can be cleared by antibodies 65 and neutrophils 67 and are susceptible to antibiotics 69. Neutrophils are attracted to the dental plaque biofilm 61. Phagocytosis is frustrated yet phagocytic enzymes 71 are released which damage host tissue around the dental plaque biofilm 61.

Accordingly, the present invention provides methods and compositions for the disruption and inhibition of dental plaque or bacterial biofilms at periodontal treatment sites. Specifically, in a first aspect, the present invention provides a method of treating periodontal disease comprising microencapsulating an agent which can disrupt dental plaque or bacterial biofilm and inserting the microparticles into a periodontal pocket lesion to allow the host immune system to more properly react against the bacterial cells.

In a second aspect, the present invention provides a method of preventing the re-emergence of the bacterial biofilm by insertion of microparticles containing an agent which inhibits biofilm formation into a periodontal pocket lesion. This could be done directly following scaling and root planing (mechanical disruption of the biofilm).

In a third aspect, the present invention provides a method of inhibiting key periodontal pathogens from inhabiting the biofilm by insertion of microparticles containing an inhibitor of one or more specific bacteria into the periodontal pocket lesion. Examples of desired periodontal pathogens to inhibit include *Porphyromonas gingivalis, Bacteroides forsythus* and *Actinobacillus actinomycetemcomitans*. This could also be done directly following scaling and root planing.

In an embodiment, the present invention includes a method of local delivery of bacterial biofilm inhibitor or disruptor agents to localized sites in the mouth. This is for treatment of periodontal disease. The method includes the steps of insertion of biodegradable microparticles containing these agents into the periodontal pocket. The method also includes allowing the microparticles to degrade and release the agents in a controlled, sustained manner. In an embodiment, insertion of biodegradable microshapes is accomplished using a syringe apparatus or hand delivery device. In an embodiment, the agents inhibit or disrupt the glycocalyx matrix of the bacterial biofilm. In an embodiment, the agents are antagonists of acylated homoserine lactones. In an embodiment, the agents are furanones or furanone derivatives. In an embodiment, the agents inhibit specific bacteria from inhibiting the bacterial biofilm. In an embodiment, the agents bind with or inhibit bacterial lipopolysaccharide. In an embodiment, the agents are histatin analogues. In an embodiment, other chemotherapeutic agents are microencapsulated and combined with microencapsulated bacterial biofilm inhibitors or disruptors for insertion into the periodontal pocket. In an embodiment, the combining step includes selecting the chemotherapeutic agent from the group consisting of antibiotics, anti-inflammatory agents and anticollagenolytic agents. In an embodiment, the biodegradable microparticles are configured as microspheres between 10 and 700 microns in diameter.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "adapted and configured" describes a system, apparatus, or other structure that is constructed or configured to perform a particular task or adopt a particular configuration to. The phrase "adapted and configured" can be used interchangeably with other similar phrases such as arranged and configured, constructed and arranged, adapted, constructed, manufactured and arranged, and the like.

All publications and patent applications in this specification are indicative of the level of ordinary skill in the art to which this invention pertains.

It is to be understood, however, that even though numerous characteristics and advantages of the invention have been set forth in the foregoing description, together with details of the structure and function of the invention, the disclosure is illustrative only, and changes may be made in detail, especially in matters of shape, size and arrangement of parts within the principle of the invention, to the full extent indicated by the broad general meaning of the terms in which the appended claims are expressed.

I claim:

1. A method of delivering an agent that disrupts biofilm to a localized site in the mouth comprising:
    inserting into a periodontal pocket a composition comprising the agent that disrupts biofilm;
    the agent that disrupts biofilm being contained within a biodegradable microparticle;
    the agent that disrupts biofilm being a furanone biofilm disrupter.

2. The method of claim 1, wherein the furanone biofilm disrupter has Formula 1, 2, 3, 4, or 5:

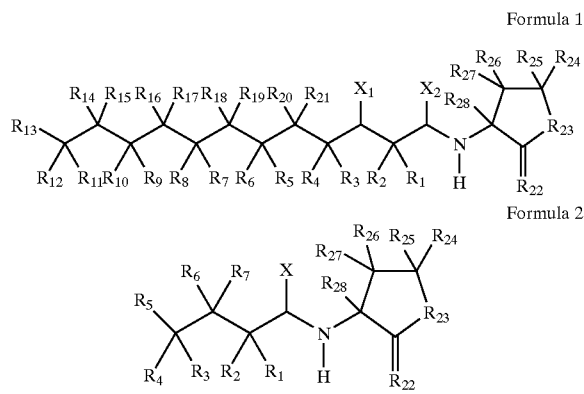

Formula 1

Formula 2 wherein: $R_1$–$R_2$, are independently H, $C_1$–$C_4$ alkyl group, OH, $NH_2$, SH, or halogen; $R_{22}$ and $R_{23}$ are independently H, S, O, NR, or NH); $R_{24}$–$R_{28}$ are independently H or halogen; and X, $X_1$, and $X_2$ are independently O, S, $H_2$, or any combination of H plus one halogen or two halogens when one or more R groups is substituted;

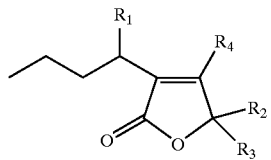

Formula 3 wherein, $R_1$, $R_2$ and $R_3$ are independently hydrogen, hydroxyl, alkyl containing from 1 to 10 carbon atoms, ether containing from 1 to 10 carbon atoms, ester containing from 1 to 10 carbon atoms, or halogenated alkene containing from 1 to 10 carbon atoms; or $R_2$ and $R_3$ together are unsubstituted or halogenated alkene containing from 1 to 10 carbon atoms and $R_4$ is hydrogen or halogen;

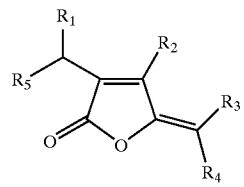

Formula 4 wherein, $R_1$ is hydrogen, hydroxyl, acetoxy, ester or ether; $R_2$ is Br or H; $R_3$ and $R_4$ are independently hydrogen or halogen; and $R_5$ is $C_1$, $C_3$, $C_5$, or $C_{11}$ alkyl; or

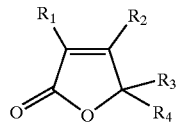

Formula 5 wherein, $R_1$, $R_2$, $R_3$ and $R_4$ are each independently hydrogen, halogen, hydroxyl, methyl, alkyl, ether or ester.

3. The method of claim 1, wherein the microparticles degrade and release the agent that disrupts biofilm in a controlled, sustained manner.

4. The method of claim 1, wherein the biodegradable microparticles comprise microspheres of diameter between 10 and 700 microns.

5. A method of delivering an agent that disrupts biofilm to a localized site in the mouth comprising:
    inserting into a periodontal pocket a composition comprising the agent that disrupts biofilm;
    the agent that disrupts biofilm being contained within a biodegradable microparticle;
    the agent that disrupts biofilm being an inhibitor of autoinducer-2; an agent that inhibits or disrupts the glycocalyx matrix of the bacterial biofilm; iron saturated lactoferrin; or a gingipain inhibitor.

6. The method of claim 5, wherein the agent is a gingipain inhibitor designated in the scientific literature as DX-9065a.

7. The method of claim 5, wherein the microparticles degrade and release the agent that disrupts biofilm in a controlled, sustained manner.

8. The method of claim 5, wherein the biodegradable microparticles comprise microspheres of diameter between 10 and 700 microns.

* * * * *